US012742148B2

(12) United States Patent
Huang et al.

(10) Patent No.: US 12,742,148 B2
(45) Date of Patent: Sep. 22, 2026

(54) APPLICATION OF ALKALI-TOLERANT MICROBIAL BACTERIA PDC-1 AND ITS IN-SITU REMEDIATION OF ORGANIC CONTAMINATED SOIL IN MINING AREAS

(71) Applicant: CHINESE RESEARCH ACADEMY OF ENVIRONMENTAL SCIENCES, Beijing (CN)

(72) Inventors: Caihong Huang, Beijing (CN); Beidou Xi, Beijing (CN); Wei Li, Beijing (CN); Yuqian Li, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 198 days.

(21) Appl. No.: 18/581,156

(22) Filed: Feb. 19, 2024

(65) Prior Publication Data

US 2025/0051713 A1 Feb. 13, 2025

(30) Foreign Application Priority Data

Feb. 20, 2023 (CN) ......................... 202310132355.5

(51) Int. Cl.
*B09C 1/10* (2006.01)
*C02F 3/34* (2023.01)
*C12N 1/20* (2006.01)
*C12R 1/385* (2006.01)

(52) U.S. Cl.
CPC .................. *C12N 1/20* (2013.01); *B09C 1/10* (2013.01); *C02F 3/34* (2013.01); *C12N 2500/05* (2013.01); *C12N 2500/34* (2013.01); *C12N 2500/74* (2013.01); *C12N 2500/76* (2013.01); *C12R 2001/385* (2021.05)

(58) Field of Classification Search
CPC ........................................................ B09C 1/10
See application file for complete search history.

(56) References Cited

FOREIGN PATENT DOCUMENTS

CN 116042484 B * 6/2023 .............. C02F 3/344

OTHER PUBLICATIONS

Medić A et a. Efficient biodegradation of petroleum n-alkanes and polycyclic aromatic hydrocarbons by polyextremophilic Pseudomonas aeruginosa san ai with multidegradative capacity. RSC Adv. Apr. 7, 2020;10(24):14060-14070. doi: 10.1039/c9ra1 (Year: 2020).*
Medić A et a. Efficient biodegradation of petroleum n-alkanes and polycyclic aromatic hydrocarbons by polyextremophilic Pseudomonas aeruginosa san ai with multidegradative capacity. RSC Adv. Apr. 7, 2020;10(24):14060-14070. doi: 10.1039/c9ra1 (Year: 2020) (Year: 2020).*

* cited by examiner

*Primary Examiner* — Heather Calamita
*Assistant Examiner* — Pricila Hauk Teodoro
(74) *Attorney, Agent, or Firm* — SZDC Law PC

(57) ABSTRACT

A method for remediating polycyclic aromatic hydrocarbons polluted and/or heavy metal polluted water or soil remediation includes: preparing a bacterial suspension containing an alkali resistant microbial strain PDC-1, the alkali-tolerant microbial bacterium PDC-1 belonging to *Pseudomonas aeruginosa* and deposited in China General Microbiological Culture Collection Center under deposit number CGMCC NO25957; and applying the bacterial suspension to water or soil contaminated with polycyclic aromatic hydrocarbons and/or heavy metals for remediation. The polycyclic aromatic hydrocarbons are naphthalene, phenanthrene, anthracene and/or pyrene.

5 Claims, 5 Drawing Sheets

APPLICATION OF ALKALI-TOLERANT MICROBIAL BACTERIA PDC-1 AND ITS IN-SITU REMEDIATION OF ORGANIC CONTAMINATED SOIL IN MINING AREAS

This application claims priority to Chinese Patent Application No. CN 202310132355.5, filed on Feb. 20, 2023, which is incorporated by reference for all purposes as if fully set forth herein.

TECHNICAL FIELD

The present invention belongs to the field of organic pollutant degradation, specifically relates to an alkali-resistant microbial bacterium PDC-1 and its application of in situ remediation of organic polluted soil in mining areas.

Technology Background

Polycyclic aromatic hydrocarbons (PAHs) are kind of persistent organic pollutants and are widely available hydrophobic aromatic compounds. The sources of PAHs are mainly divided into two categories: anthropogenic sources and natural sources and anthropogenic sources are the main sources of PAH pollution in the environment. In highly contaminated soils, PAHs come mainly from accidental spills of petroleum or from the petrochemical, steelmaking, and coal industries. Sixteen PAHs are classified as priority pollutants by the U.S. Environmental Protection Agency and have received widespread attention, because most of them are proven carcinogens. Due to their toxicity and persistence in the environment, there is an urgent need for the remediation of PAH-contaminated soils.

China is the largest consumer of coal in the world. The mining of coal for industrial production is one of the main sources of soil PAH pollution. The transportation, processing and stockpiling in the mining area cause pollution of the soil. The coal gangue is by-product of coal mining, through which a large number of organic pollutants and heavy metal pollutants are discharged into the environment.

Microbial degradation technology is recognized as a green, efficient, and low-cost remediation method in organic pollution remediation. *Pseudomonas aeruginosa* belongs to the genus *Pseudomonas*, is one of the microorganisms with good application prospects in bioremediation applications, and has good degradation ability to refractory substances such as aromatic compounds and organic pesticides. However, the contaminated soil in the mining area are usually composite pollution systems with both organic contaminants and heavy metals. Conventional bioremediation methods have great limitations in the field application, because heavy metals are toxic, affecting the activity of degrading bacteria. Therefore, heavy metal tolerance is an important criterion in addition to the microorganisms' degradation ability of organic pollutants when the bioremediation is performed.

Contents of the Invention

The first objective of the present invention is to provide a strain of alkali-resistant microbial bacterium PDC-1.

In order to achieve the above purpose, the present invention provides an alkali-resistant microbial bacteria PDC-1, and the strain belongs to *Pseudomonas aeruginosa*, and deposited in the China General Microbiological Culture Collection Center (deposit number CGMCC NO25957) on Dec. 24, 2022.

The strain was isolated from the soil of a coal gangue stockpile at a coal mine in Xintai City, Shandong Province. Strain PDC-1 is a gram-negative bacterium, and the colony on the LB solid plate is round, light green, and the surface is raised, smooth and moist.

The invention also provides a culture of the microbial bacterium PDC-1 or a culture after passage cultivation.

The invention also provides the application of the microbial bacterium PDC-1 in the remediation of polycyclic aromatic hydrocarbons polluted and/or heavy metal polluted water or soil.

Specifically, the polycyclic aromatic hydrocarbons are selected from naphthalene, phenanthrene, anthracene and/or pyrene; the polycyclic aromatic hydrocarbons are selected from one or more of naphthalene, phenanthrene, anthracene, pyrene, benzo[a]pyrene, and benzo[g,h,i]perylene; the heavy metals are heavy metals such as cadmium, chromium, and antimony. More preferably, the bacterial suspension of the composite pollution remediation bacteria is applied to the soil.

The present invention also provides the cultivation method of described alkali-resistant microbial bacterium PDC-1, which is characterized in that:

S1. The solid inorganic salt medium containing polycyclic aromatic hydrocarbon liquor is incubated on plates at 30-35° C. for about 48-72 hours;

S2. Pick a single colony and inoculate it into LB liquid medium, and after shaking at 150-180 rpm at 30-35° C., prepare a bacterial suspension with $OD_{600}$=0.5-1.5;

S3. Inoculate the bacterial suspension into a fermentation medium and ferment at 30-35° C. with 150-180 rpm for 48-72 hours to obtain the culture medium.

Preferably, the fermentation medium formula is corn oil 20 g/L, glucose 5 g/L, yeast powder 5 g/L, $NaNO_3$ 35 g/L, NaCl 5 g/L, $K_2HPO_4$ 2 g/L, distilled water 1 L.

In addition, preferably, the number of cells in the degrading agent is not less than $1.0\times10^8$ CFU/mL, preferably $1.0\times10^9$ CFU/mL to $1.0\times10^{10}$ CFU/mL.

In a specific embodiment, the present invention also provides a preparation method for polycyclic aromatic hydrocarbon-degrading agent of strain PDC-1:

(1) After coating the solid inorganic salt medium containing polycyclic aromatic hydrocarbon mother liquor, it was incubated at 30-35° C. for 48-72 h, and a single colony with a diameter of 1-2 mm was seen.

(2) Pick a single colony and inoculate it into LB liquid medium, and then incubate it at 150-180 rpm at 30-35° C. to prepare an $OD_{600}$=1 bacterial suspension.

(3) Inoculate 10% of the inoculum into the fermentation medium, and then fermented at 150-180 rpm at 30-35° C. shaking for 72 h, the culture medium is obtained as a degrading agent for the degradation of polycyclic aromatic hydrocarbons.

The inorganic salt culture medium is: $Na_2HPO_4$ 2800 mg, $(NH_4)_2SO_4$ 500 mg, $CuCl_2\cdot2H_2O$ 0.001 mg, $H_3BO_3$ 0.03 mg, $FeSO_4\cdot7H_2O$ 0.2 mg, $MnCl_2\cdot4H_2O$ 0.003 mg, $NiCl_2\cdot6H_2O$ 0.002 mg, $KH_2PO_4$ 1000 mg, $Na_2EDTA$ 0.5 mg, $CoCl_2\cdot6H_2O$ 0.02 mg, $ZnSO_4\cdot7H_2O$ 0.01 mg, $Na_2MoO_4\cdot2H_2O$ 0.003 mg, distilled water 1 L.

The formula of the LB medium is peptone 10 g/L, yeast extract powder 5 g/L, NaCl 10 g/L, distilled water 1 L, pH 7.0-7.2.

The formula of the fermentation medium is corn oil 20 g/L, glucose 5 g/L, yeast powder 5 g/L, $NaNO_3$ 5 g/L, NaCl 5 g/L, $K_2HPO_4$ 2 g/L, distilled water 1 L, pH 7.2-7.5.

The present invention also provides a degrading microbial agent for degrading polycyclic aromatic hydrocarbons containing the alkali-resistant microbial bacterium PDC-1.

Preferably, the microbial bacterium PDC-1 exists in the form of a bacterial suspension.

Further, the culture medium obtained according to the culture method described above is used as the bacterial suspension.

The present invention enriches and screens out the strain of *Pseudomonas aeruginosa* from the soil sample of the coal gangue stockpile in the coal mine areas, which has good activity and metabolic ability in both neutral and alkaline environments, and has good activity and metabolic ability in the typical polycyclic aromatic hydrocarbonsnaphthalene, phenanthrene, anthracene, pyrene, benzo[a]pyrene, and benzo[g,h,i]perylene and others have good degradation ability, and at the same time, it has a good tolerance to heavy metal $Cd^{2+}$, and the degradation rate of more than 60% is achieved in the soil with a concentration of $Cd^{2+}$20 mg/kg, indicating that the strain PDC-1 can not only repair the water contaminated by polycyclic aromatic hydrocarbons, but also be used in the soil polluted by heavy metals and polycyclic aromatic hydrocarbons to achieve the degradation of polycyclic aromatic hydrocarbons in different environments.

BIOMATERIAL PRESERVATION INFORMATION

Figure 1:
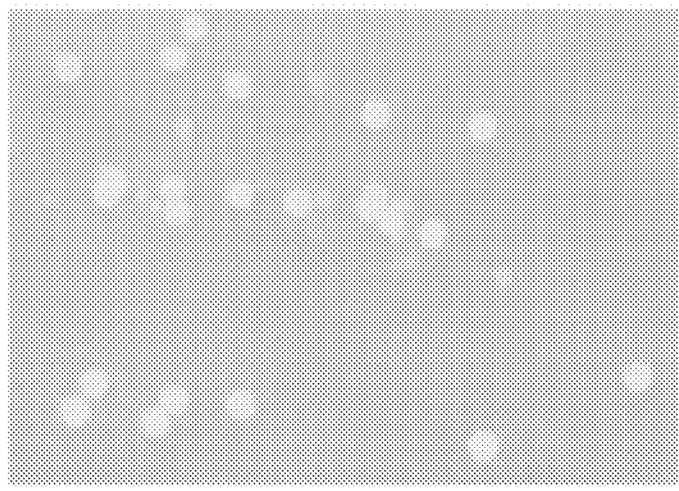
FIG. 1 is the colony morphology of the PDC-1 plate of the present invention.

Microbial bacterium PDC-1, with a deposit number CGMCC NO25957, taxonomic named *Pseudomonas aeruginosa*, deposited in the China General Microbiological Culture Collection Center (abbreviated as CGMCC) on Oct. 24, 2022. The address of the depositary unit: No. 3, Courtyard 1, Beichen West Road, Chaoyang District, Beijing.

SPECIFIC EMBODIMENTS

The present invention is further illustrated below in conjunction with the drawings of the description and specific embodiments.

Embodiment 1: Isolation and Identification of PDC-1

1. Sample Source

Soil was collected from the polluted site of coal gangue stockpile in Shandong coal mine, and the high-concentration phenanthrene was used as the carbon source for long-term acclimation, and the efficient phenanthrene degrading bacteria were obtained through multiple screening, separation, and purification.

2. Culture Medium 2.1 Inorganic Salt Medium

Inorganic salt medium is used for microbial culture of samples, pure bacteria, and polycyclic aromatic hydrocarbon degradation experiments under microbial agent conditions. The medium formulation is shown in Table 1. The preparation method is to add each component to distilled water, stir and mix, adjust the pH to 7.2-7.5, and sterilize.

TABLE 1

Inorganic salt medium formulations

| Name of the reagent | Concentration (mg/L) |
|---|---|
| $Na_2HPO_4$ | 2800 |
| $(NH_4)_2SO_4$ | 500 |
| $CuCl_2$•$2H_2O$ | 0.001 |
| $H_3BO_3$ | 0.03 |
| $FeSO_4$•$7H_2O$ | 0.2 |
| $MnCl_2$•$4H_2O$ | 0.003 |
| $NiCl_2$•$6H_2O$ | 0.002 |
| $KH_2PO_4$ | 1000 |
| $Na_2EDTA$ | 0.5 |
| $CoCl_2$•$6H_2O$ | 0.02 |
| $ZnSO_4$•$7H_2O$ | 0.01 |
| $Na_2MoO_4$•$2H_2O$ | 0.003 |

2.2 Nutrient Medium

The types and components of liquid nutrient medium used in this experiment are shown in Tables 2 and 3. The corresponding solid medium is the original medium formulation, and 12-15 g/L agar powder is added. If the culture conditions of the strain are not specified, the pH of the medium is adjusted to 7.2-7.5. The preparation method is to add each component to water, stir and mix well, and sterilize at 121° C. for 15 minutes at high temperature and humidity heat.

TABLE 2

LB medium components

| Name of the reagent | Concentration (g/L) |
|---|---|
| peptone | 10 |
| Yeast extract powder | 5 |
| NaCl | 10 |

TABLE 3

Composition of fermentation medium

| Name of the reagent | Concentration (g/L) |
|---|---|
| corn oil | 20 |
| glucose | 5 |
| $NaNO_3$ | 5 |
| Yeast extract powder | 5 |

TABLE 3-continued

| Composition of fermentation medium | |
|---|---|
| Name of the reagent | Concentration (g/L) |
| $K_2HPO_4$ | 2 |
| NaCl | 5 |

3. Acclimation, Screening, and Isolation of Strains

The collected contaminated soil was added to the sterilized inorganic salt medium with a mass ratio of 1:10 and incubated at 150-180 rpm and 30-35° C. for 5 days. It was then inoculated at a concentration of 100 mg $L^{-1}$ phenanthrene and inoculated in 10% inorganic salt medium, placed in a 30° C. incubator protected from light and shaking, and the operation was repeated 3 times.

Strain acclimation is based on phenanthrene as the only carbon source in the inorganic salt medium, and 5 days is an acclimation cycle. At the end of the cycle, 10% of the inoculum volume was transferred to fresh medium of the same system and the above process was repeated three times.

The culture samples obtained above were diluted and separated by coating, and the samples were separated with inorganic salt medium containing 100 mg/L phenanthrene. The coated samples were placed at 30° C. in the dark and cultured for 1-2 days, and a number of single colonies with differences were selected according to the morphology, size, color, transparency and other characteristics of the colonies, and purified and cultured on the nutrient medium plate. Purified single colonies were picked for storage.

4. Strain Identification

Figure 2:
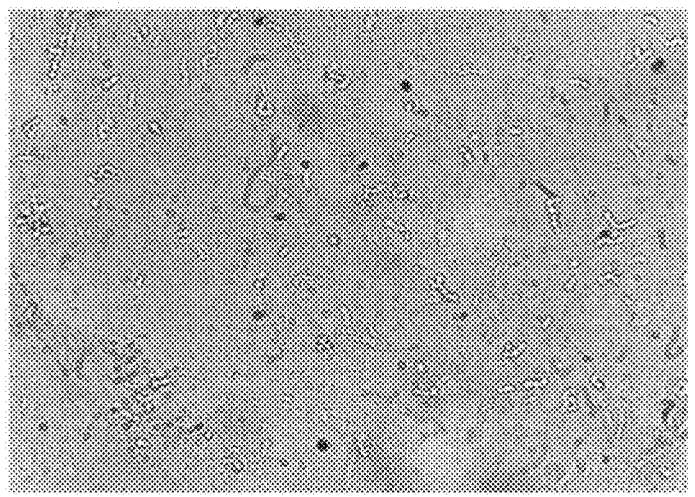
FIG. 2 is the cell morphology of PDC-1 of the present invention.

According to the results of Gram staining reaction, morphological and physiological characteristics of the strains, the strains were preliminarily identified. The plate colony morphology of the strain PDC-1 is shown in FIG. 1, and the morphology under light microscopy is shown in FIG. 2. Its main biological characteristics: the thallus is short rod-shaped, gram-negative bacilli, and the colonies on the LB solid plate are round, light green, and the surface is raised, smooth, and the edges are irregular and opaque.

Figure 3:
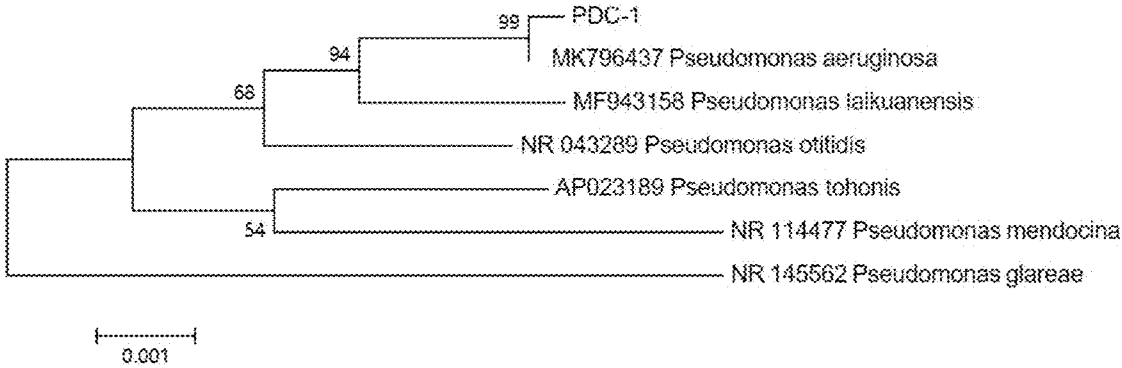
FIG. 3 shows the PDC-1 phylogenetic tree based on the homology of the 16S rRNA gene sequence.

Strain 16S rDNA Identification: Single colony lysis was used as template by PCR with primers. The PCR reaction conditions were: pre-denaturation at 94° C. for 5 min, denaturation at 94° C. for 30 s, annealing at 54° C. for 30 s, extension at 72° C. for 1 min 30 s, 24 cycles, and finally extension at 72° C. for 10 min. The 16S rRNA gene sequence was sequenced and compared with the NCBI library, and the homology of the strain PDC-1 and *Pseudomonas aeruginosa* was 99.93%, indicating that the strain was *Pseudomonas*. The phylogenetic tree is constructed as shown in FIG. 3.

Embodiment 2: PDC-1 Polycyclic Aromatic Hydrocarbon Degradation Experiment

1. Preparation of Microbial Agent (1) Pick the purified single colonies in the plate and inoculate them into LB liquid medium, and prepare an $OD_{600}$=1 bacterial suspension at 30° C. at 180 rpm shaking culture.

(2) Inoculate 10% of the bacterial suspension into a new fermentation medium, and fermented at 180 rpm at 30° C. shaking for 72 h, and the concentration of the fermentation broth was detected to be $10^{8-10}$ CFU/mL, and the obtained fermentation broth was PDC-1 liquid inoculum.

2. Microbial Agent Degradation of Phenanthrene 2 mL of the prepared PDC-1 liquid inoculant was inoculated into 50 mL of inorganic salt medium containing 50 mg/L phenanthrene, with phenanthrene as the only carbon source, the medium was placed in a constant temperature shaker at 30° C. for culture, and the control group was not inoculated with fungicide, and a total of 3 groups of repeated experiments were set up, and the phenanthrene concentration and $OD_{600}$ in the medium were measured every day.

Figure 4:
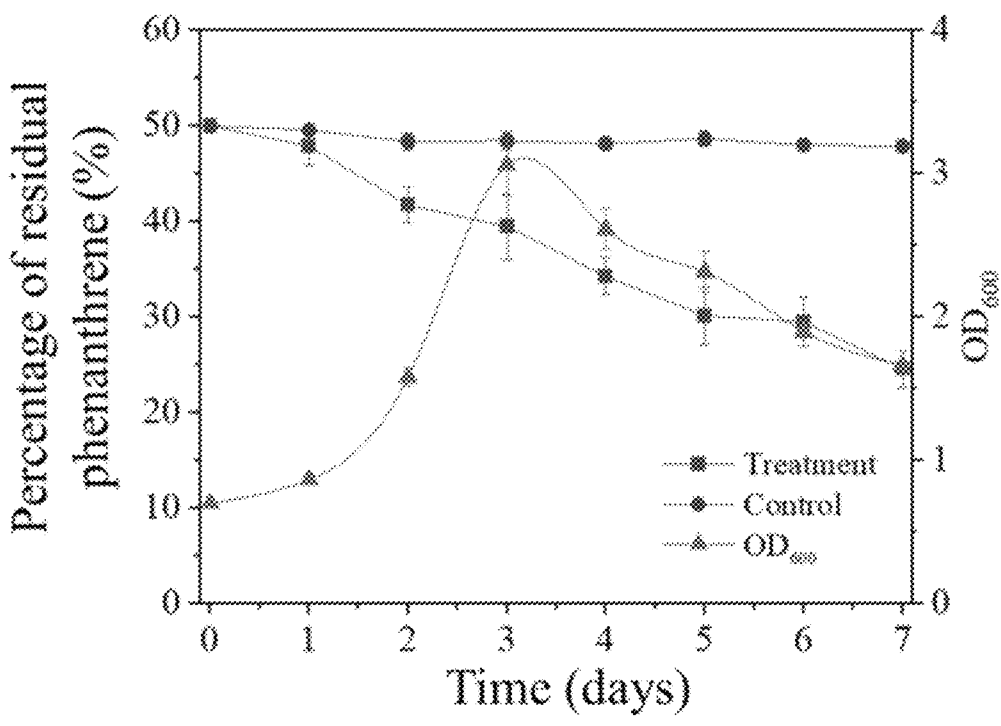
FIG. 4 is the degradation kinetic curve of PDC-1 to phenanthrene of the present invention.
Figure 5:
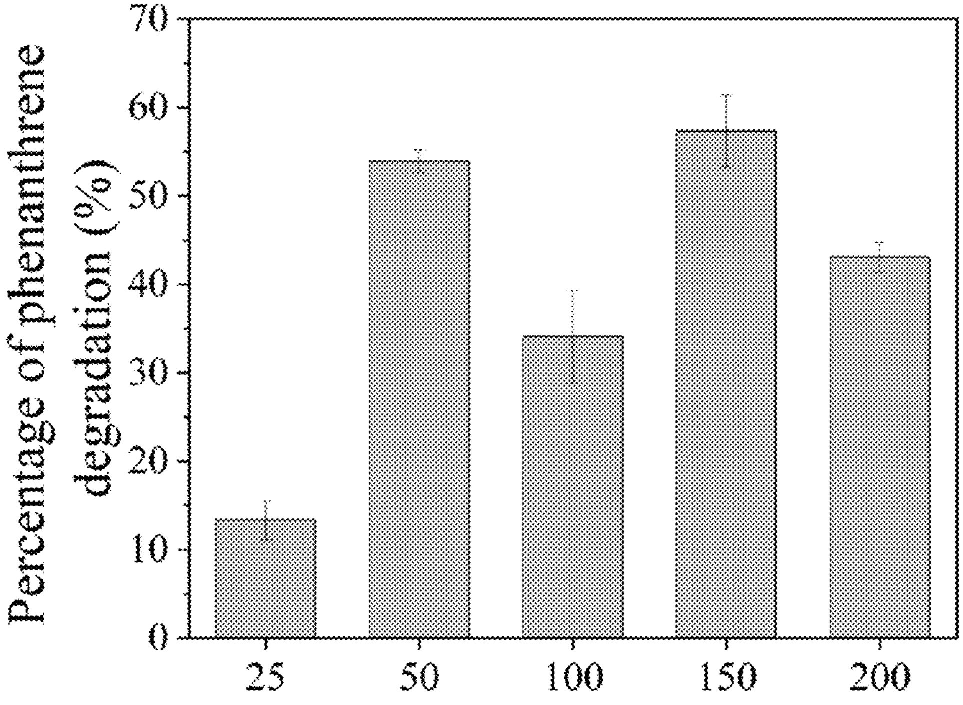
FIG. 5 is the degradation ability of PDC-1 to different concentrations of phenanthrene of the present invention.

Add 20 mL of chromatographic pure n-hexane to the conical flask of the culture medium, sealed and shaken at 200 rpm for 30 min, then, liquid-liquid extraction is carried out through a separating funnel to separate and collect n-hexane, and repeated twice. All the collected n-hexane extract was concentrated by nitrogen blowing instrument, the volume was fixed to 10 mL, 1 mL of nitrogen was blown to nearly dry, and then the volume was fixed to 1 mL with chromatography pure methanol through a 0.22 μm filter membrane, loaded into a brown liquid phase vial, and the concentration of polycyclic aromatic hydrocarbons was determined by the method of high performance liquid chromatography (HJ 478-2009). The determination of $OD_{600}$ was to take 1 mL of solution when the UV spectrophotometer was adjusted to 600 nm, and the initial inorganic salt containing phenanthrene was zeroed out, and then the sample was determined. The degradation kinetics and growth curves of phenanthrene after the addition of inoculants are shown in FIG. 4, and the bacterial density of the medium reached the highest on 2 days and degraded to less than 25 mg/L after 6 days.

3. Phenanthrene Degradation Under Different Conditions in Liquid Medium 2 mL of PDC-1 liquid inoculant was inoculated into 50 mL of inorganic salt medium containing 25 mg/L, 50 mg/L, 100 mg/L, 150 mg/L and 200 mg/L phenanthrene, respectively, and the medium was placed in a constant temperature shaker at 30° C. for 180 rpm. The phenanthrene concentration in the medium is determined after 6 days and the assay is repeated 3 times. The degradation rate of PDC-1 microbial agent was higher with 54% and 57% at the phenanthrene concentrations of 50 mg/L and 150 mg/L, respectively.

Figure 6:
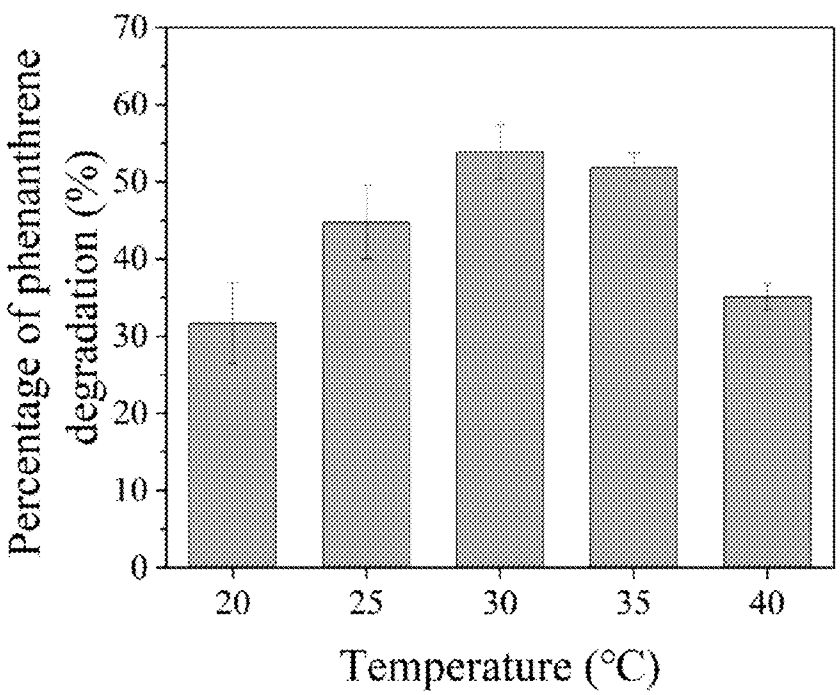
FIG. 6 is the degradation ability of PDC-1 to phenanthrene at different temperatures of the present invention.

2 mL of the prepared PDC-1 liquid inoculant was inoculated into 50 mL of inorganic salt medium containing 50 mg/L phenanthrene, and the medium was placed in a constant temperature shaker at 20° C., 25° C., 30° C., 35° C. and 40° C. for 180 rpm, and the phenanthrene concentration in the medium was measured after 6 days, and the determination was repeated 3 times. The degradation rate of phenanthrene at different temperatures is shown in FIG. 6, and the degradation effect of microbial agent is better at 30-35° C., and the degradation rate is maintained at more than 50%.

Figure 7:
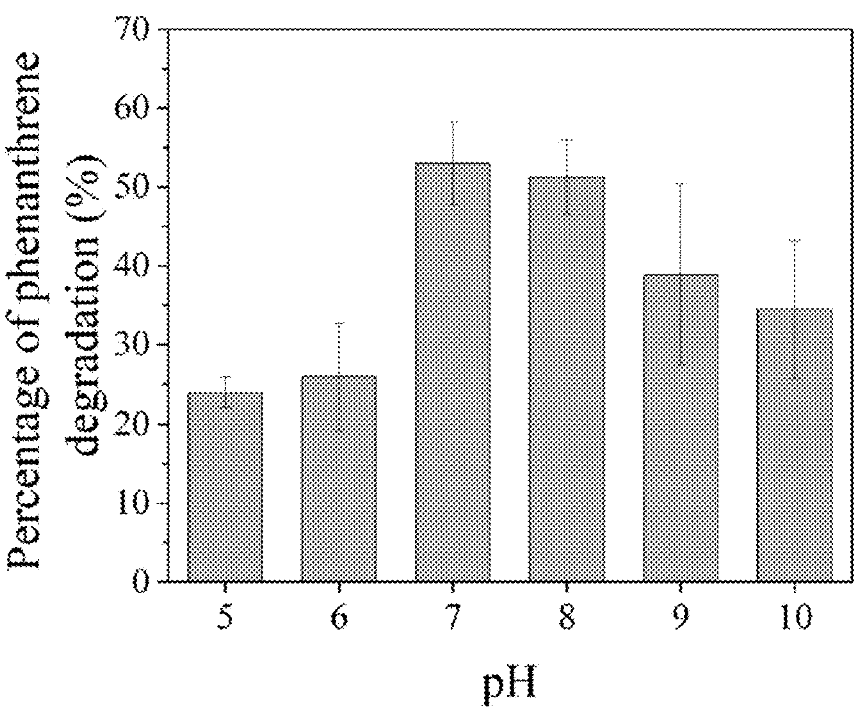
FIG. 7 is the degradation ability of PDC-1 to phenanthrene at different pH values of the present invention.

The pH value of 50 mL of inorganic salt medium containing 50 mg/L phenanthrene was adjusted to 5, 6, 7, 8, 9, 10 respectively, and 2 mL of PDC-1 liquid inoculant was inoculated into these mediums, placed in a constant temperature shaker at 30° C. for 180 rpm for incubation, and the phenanthrene concentration in the medium was measured after 6 days, and the determination was repeated 3 times. The degradation rate of phenanthrene under different pH values is shown in FIG. 7, when the pH value of the medium is between 7 and 8, the degradation rate of the microbial agent is the highest, which is maintained at 50%-53%, and when the pH reaches 10, the microbial agent can still achieve about 30% degradation rate.

Figure 8:
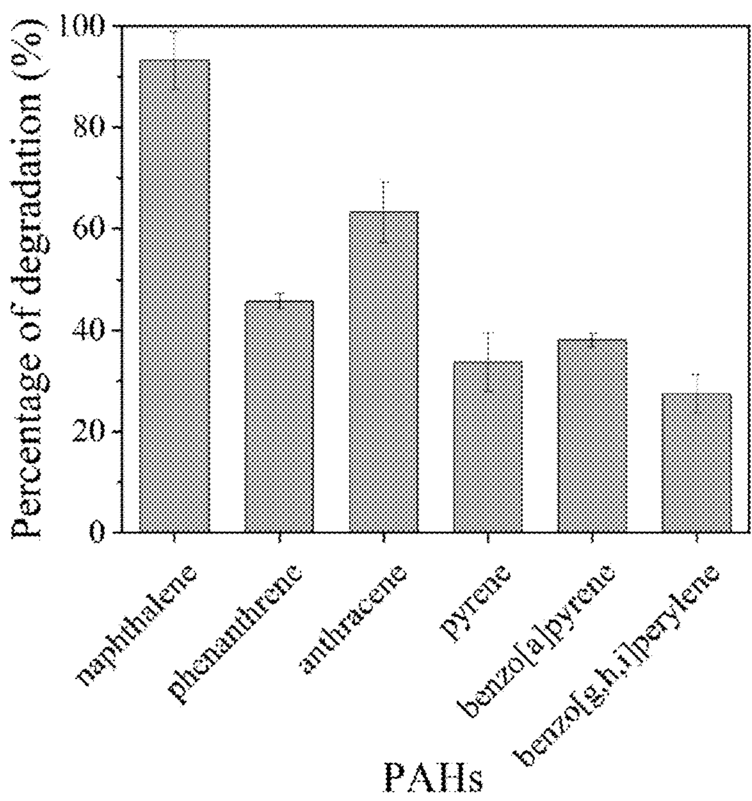
FIG. 8 is the degradation capacity of PDC-1 to different 6 typical polycyclic aromatic hydrocarbons of the present invention.

50 mL of inorganic salt medium containing naphthalene 50 mg/L, phenanthrene 50 mg/L, anthracene 50 mg/L, pyrene 20 mg/L, benzo[a]pyrene 20 mg/L, and benzo[g,h,i]perylene 20 mg/L was prepared, and 2 mLPDC-1 inoculants were inoculated into the medium and placed in a constant temperature shaker at 30° C. for 180 rpm for culture, and the concentration of polycyclic aromatic hydrocarbons in the medium was measured after 6 days, and the determination was repeated 3 times. The degradation rates of six PAHs by PDC-1 are shown in FIG. 8, and the degradation rates of the six PAHs are 93.2% naphthalene, 45.8% phenanthrene, 63.2% anthracene, 33.7% pyrene, 38.1% benzo[a]pyrene, and 27.5% benzo[g,h,i]perylene, respectively.

Figure 9:
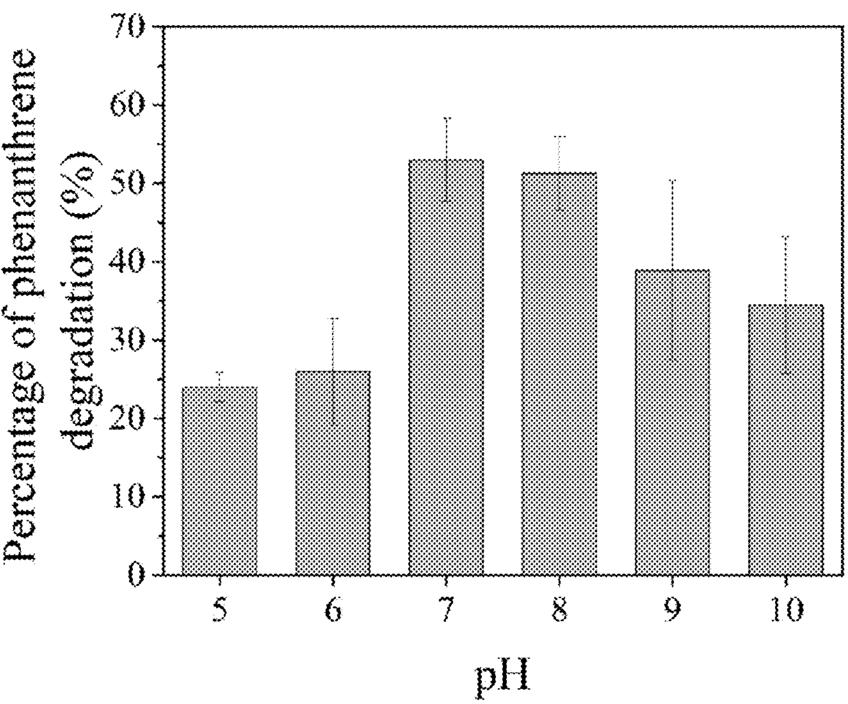
FIG. 9 is the degradation ability of PDC-1 to phenanthrene at different $Cd^{2+}$ concentrations of the present invention.

50 mL of inorganic salt medium containing 50 mg/L phenanthrene was prepared, and 0.8 mL, 1.6 mL, 3.2 mL, and 4.8 mL of $CdCl_2$ solution with a concentration of 10 g/L were added to each medium to make $Cd^{2+}$ concentrations were 5 mg/L, 10 mg/L, 20 mg/L, 40 mg/L, and then 2 mL PDC-1 microbial agent was added to each medium, placed in a constant temperature shaker at 30° C. for 180 rpm for culture, and the phenanthrene concentration in the medium was measured after 6 days, and the measurement was repeated 3 times. The degradation rate of PDC-1 at different $Cd^{2+}$ concentrations is shown in FIG. 9, when the concentration of $Cd^{2+}$ is <5 mg/L, the metabolic activity of the microbial agent is not inhibited, and the degradation rate is maintained at more than 45%, and when the concentration of $Cd^{2+}$ reaches 20 mg/L, the degradation rate of phenanthrene is basically maintained at more than 25%.

4. Degradation of Phenanthrene Under Different Conditions in Contaminated Soil

Experimental setup: The soil was selected and mixed evenly after passing through a 10-mesh sieve. 20 mg of phenanthrene was dissolved in 10 mL of acetone and added to 100 g of soil to prepare 200 mg/kg of phenanthrene contaminated soil subsample, and 1.6 mL of $CdCl_2$ solution with a concentration of 10 g/L was added to 10 g of soil to prepare 1 g/kg of $Cd^{2+}$ contaminated soil subsample. 86-90 g of soil, 10 g of phenanthrene contaminated soil subsample and 1-4 g of $Cd^{2+}$ contaminated soil subsample were added to the beaker, and the contaminated soil with phenanthrene concentration of 20 mg/kg and $Cd^{2+}$ concentration of 10 mg/kg, 20 mg/kg and 40 mg/kg was prepared evenly. 5 mL PDC-1 microbial agent was added to 100 g of contaminated soil and mixed evenly to keep the moisture content at about 20%, and it was placed in a constant temperature incubator at 30° C. for 20 days, and soil samples were taken at intervals of 10 days to determine the concentration of phenanthrene.

Determination of phenanthrene concentration in soil: PAHs in soil were extracted according to the National Environmental Protection Standard of the People's Republic of China "Determination of Polycyclic aromatic hydrocarbons in soil and sediment by high performance liquid chromatography." 5 g of soil samples were weighed for freeze-drying, 15 mL of acetone-n-hexane (1:1) mixed solution was added after grinding through a 60-mesh sieve, sealed and soaked in the dark for 8 hours, then ultrasonic treatment for 30 min, and then centrifugation poured out the solution, and the extraction was repeated 3 times. The extract was mixed and concentrated to about 1 mL by nitrogen blowing, and purified by magnesium silicate solid-phase extraction column. The purified eluent was nitrogen-blown again and concentrated to nearly dry, about 3 mL of methanol was added, and repeated three times to the final volume was 1 mL. The determination was performed by high-performance liquid chromatography with a sample volume of 10 μL, a column temperature of 35° C., a mobile phase of A Methanol:B water (80:20), and a detection wavelength of 252 nm.

Figure 10:
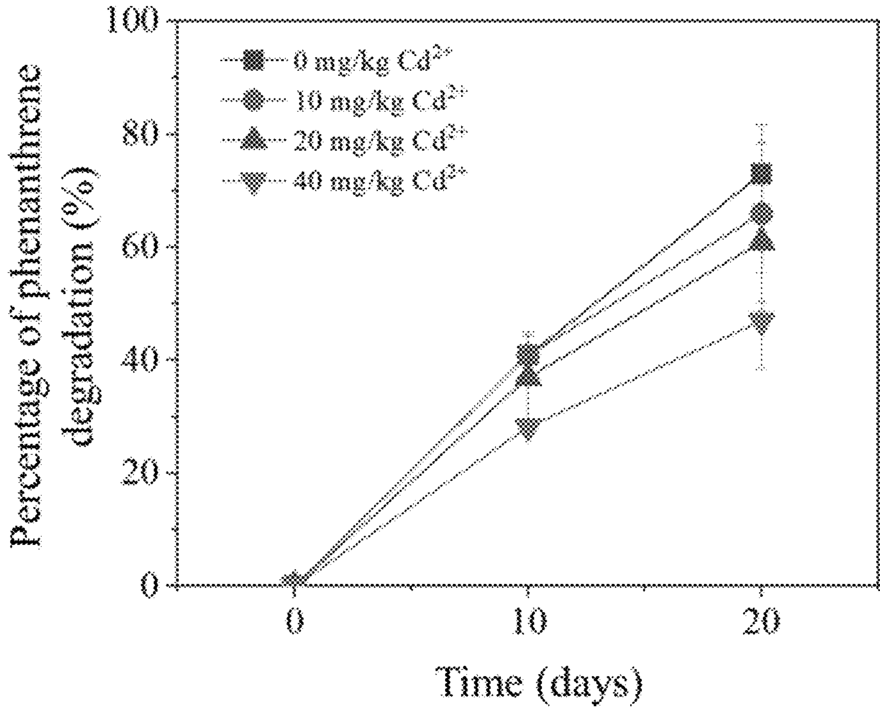
FIG. 10 is the degradation ability of PDC-1 to phenanthrene in soil with different $Cd^{2+}$ concentrations of the present invention.

The degradation rate of phenanthrene in soil with different $Cd^{2+}$ concentrations is shown in FIG. 10, when the soil $Cd^{2+}$ concentration ≤20 mg/kg, the microbial activity was not significantly inhibited, and the degradation rate of phenanthrene in the soil was maintained at 61%-73%, and when the soil $Cd^{2+}$ concentration reached 40 mg/kg, the metabolic activity was inhibited and the degradation rate was achieved down to about 47%.

The above is only the preferred embodiment of the present invention, and it should be noted that the preferred embodiment shall not be regarded as a restriction on the present invention, and the scope of protection of the present invention shall be subject to the scope limited by the claims. For a person skilled in the art, a number of improvements and embellishments may also be made without departing from the spirit and scope of the present invention, and these improvements and embellishments shall also be regarded as the scope of protection of the present invention.

The invention claimed is:

1. A method for remediating polycyclic aromatic hydrocarbons polluted and/or heavy metal polluted water or soil remediation, comprising:

preparing a bacterial suspension containing an alkali resistant microbial strain PDC-1, the alkali-tolerant microbial bacterium PDC-1 belonging to *Pseudomonas aeruginosa* and deposited in China General Microbiological Culture Collection Center under deposit number CGMCC NO25957; and applying the bacterial suspension to water or soil contaminated with polycyclic aromatic hydrocarbons and/or heavy metals for remediation, wherein the polycyclic aromatic hydrocarbons are naphthalene, phenanthrene, anthracene and/or pyrene.

2. The method according to claim 1, wherein the polycyclic aromatic hydrocarbons are selected from the group consisting of naphthalene, phenanthrene, anthracene, pyrene, benzo[a]pyrene, and benzo[g,h,i]perylene; and the heavy metal is selected from the group consisting of cadmium, chromium, and antimony.

3. The method according to claim 1, wherein preparing the bacterial suspension comprises:

S1: incubating a solid inorganic salt medium containing polycyclic aromatic hydrocarbon liquor on plates at 30-35° C. for about 48-72 hours;

S2: picking a single colony and inoculating into LB liquid medium, and after shaking at 150-180 rpm at 30-35° C., preparing a bacterial suspension with $OD_{600}$=0.5-1.5; and S3: inoculating the bacterial suspension into a fermentation medium and fermenting at 30-35° C. with 150-180 rpm for 48-72 hours to obtain the bacterial suspension.

4. The method according to claim 3, wherein the fermentation medium comprises corn oil 20 g/L, glucose 5 g/L, yeast powder 5 g/L, $NaNO_3$ 35 g/L, NaCl 5 g/L, and $K_2HPO_4$ 2 g/L.

5. The method according to claim 4, wherein a number of bacterial cells in the bacterial suspension is not less than $1.0\times10^8$ CFU/mL.

* * * * *